(12) United States Patent
Norey et al.

(10) Patent No.: US 9,926,525 B2
(45) Date of Patent: Mar. 27, 2018

(54) CELL CULTURING AND/OR BIOMANUFACTURING SYSTEM

(71) Applicants: GE Healthcare UK Limited, Buckinghamshire (GB); Electechs Limited, Swansea (GB)

(72) Inventors: Christopher George Norey, Cardiff (GB); Michelle Louise Janas, Cardiff (GB); Anthony Patterson, Cardiff (GB); Adrian Crawley, Swansea (GB)

(73) Assignee: GE Healthcare UK Limited, Little Chalfont (GB)

( * ) Notice: Subject to any disclaimer, the term of this patent is extended or adjusted under 35 U.S.C. 154(b) by 246 days.

(21) Appl. No.: 14/767,141

(22) PCT Filed: Feb. 10, 2014

(86) PCT No.: PCT/EP2014/052551
§ 371 (c)(1),
(2) Date: Aug. 11, 2015

(87) PCT Pub. No.: WO2014/122307
PCT Pub. Date: Aug. 14, 2014

(65) Prior Publication Data
US 2015/0368600 A1 Dec. 24, 2015

(30) Foreign Application Priority Data
Feb. 11, 2013 (GB) .................................. 1302393.2

(51) Int. Cl.
*C12M 3/00* (2006.01)
*C12M 1/00* (2006.01)
(Continued)

(52) U.S. Cl.
CPC ............ *C12M 23/48* (2013.01); *C12M 23/02* (2013.01); *C12M 23/28* (2013.01); *C12M 23/44* (2013.01);
(Continued)

(58) Field of Classification Search
CPC ...... C12M 23/02; C12M 23/28; C12M 23/44; C12M 23/48; C12M 23/52; C12M 27/02;
(Continued)

(56) References Cited

U.S. PATENT DOCUMENTS 6,475,776 B1  11/2002 Higuchi
6,536,859 B1   3/2003 Bathe
(Continued)

FOREIGN PATENT DOCUMENTS

CN  202201906 U  4/2012
DE  3140079 A1   9/1982
(Continued)

OTHER PUBLICATIONS

Chinese Office Action for CN Application No. 201480008185.9 dated Aug. 17, 2016 (English translation) (7 pages).
(Continued)

*Primary Examiner* — Nathan A Bowers
*Assistant Examiner* — Lydia Edwards
(74) *Attorney, Agent, or Firm* — Eversheds Sutherland (US) LLP

(57) ABSTRACT

The present invention relates to systems and methods for optimising the usage of laboratory and cell culturing space for cell culture and biomanufacturing. The invention provides a system and method that can be used to provide a plurality of workstations and/or storage bays for bioreactors in cell culturing and/or biomanufacturing facilities.

18 Claims, 20 Drawing Sheets

(51) Int. Cl.
*C12M 1/06* (2006.01)
*C12M 1/34* (2006.01)

(52) U.S. Cl.
CPC ............ *C12M 23/52* (2013.01); *C12M 27/02* (2013.01); *C12M 29/00* (2013.01); *C12M 41/12* (2013.01)

(58) Field of Classification Search
CPC .................. C12M 29/00; C12M 41/12; H02M 2001/0077; H02M 2003/072; H02M 3/07; H05B 33/0806; H05B 33/0815; H05B 33/0818
USPC .................. 435/252.1, 254.1, 289.1, 325
See application file for complete search history.

(56) References Cited

U.S. PATENT DOCUMENTS

| | | |
|---|---|---|
| 2006/0270027 A1 | 11/2006 | Shaw |
| 2007/0113474 A1 | 5/2007 | Everett |
| 2012/0083029 A1 | 4/2012 | Tsumura |

FOREIGN PATENT DOCUMENTS

| | | |
|---|---|---|
| EP | 1238705 A | 1/2011 |
| FR | 2849862 A1 | 7/2004 |
| GB | 2402481 A | 12/2004 |
| JP | 2001299325 A | 10/2001 |
| WO | 1993012430 A | 6/1993 |
| WO | 2011130865 A2 | 10/2011 |
| WO | 2012066100 A1 | 5/2012 |

OTHER PUBLICATIONS

GB Search Report issued in connection with corresponding application No. 1302393.2 dated Aug. 8, 2013.

GB Search Report issued in connection with corresponding application No. 1302393.2 dated Sep. 26, 2013.

International Search Report and Written Opinion issued in connection with corresponding application No. PCT/EP2014/052551 dated Oct. 1, 2014.

CELL CULTURING AND/OR BIOMANUFACTURING SYSTEM

FIELD OF INVENTION

Embodiments of the present invention relate to the field of cell culture and biomanufacturing. In particular, embodiments of the present invention relate to systems and methods for optimising the usage of laboratory and cell culturing space for cell culture and biomanufacturing.

BACKGROUND OF THE INVENTION

Cell culture, for example the culture of mammalian, bacterial or fungal cells, may be carried out to harvest the living cells for therapeutic purposes and/or to harvest biomolecules, such as proteins or chemicals (e.g. pharmaceuticals) produced by the cells. The cells are generally grown in bioreactors which are sterilizable vessels designed to provide the necessary nutrients and environmental conditions required for cell growth and expansion. Conventional bioreactors have glass or metal growth chambers which can be sterilized and then inoculated with selected cells for subsequent culture and expansion. Media within the growth chambers are often agitated or stirred by the use of mechanical or magnetic impellers to improve aeration, nutrient dispersal and waste removal.

In recent years, there has been a move towards 'single use' bioreactors which offer greater production flexibility, ease of use, reduced capital cost investment and reduced risk of cross-contamination. These systems can also improve the efficiency of aeration, feeding and waste removal to increase cell densities and product yields. Examples include WAVE™ bags (GE Healthcare) mounted on rocking platforms for mixing, to the introduction of stirred-tank single-use vessels such as those available from Xcellerex (GE Healthcare).

Manufacturing facilities, such as tissue culture laboratories, for the production of cells and biomolecules, have traditionally been custom designed and carried out in clean environments to reduce the risk of contamination. Such facilities are costly to run and maintain and also to modify if priorities or work demands change. Work stations for maintaining or harvesting the cells within the bioreactors require a specific 'footprint' which occupies a significant floorspace in the culture laboratory. As the workstations spend much of their time unattended, while the cells are growing in the bioreactors, the laboratory space is not efficiently or effectively used.

There is therefore a need to optimise the usage of cell culture and laboratory space which grow cells in bioreactors for cell culture and biomanufacturing. The present invention addresses this problem and provides systems and methods that can be used to provide a plurality of workstations and/or storage bays for bioreactors.

SUMMARY OF THE INVENTION

According to a first aspect of the present invention, there is provide a system for cell culture and/or biomanufacturing comprising
   i. a base unit comprising:
      a frame supporting walls, and
      a movable platform to define a chamber therein;
   ii. a stacking unit comprising:
      a frame supporting side walls, a back wall, a ceiling and a movable platform to define an upper and a lower chamber therein,
      said lower chamber being dimensioned to receive said base unit therein;
   iii. a guard unit comprising:
      a frame supporting side walls, a movable platform and an openable front wall to define an upper and a lower chamber therein, said lower chamber being dimensioned to partially receive said stacking unit therein; and
      legs supporting said frame and dimensioned to receive the movable base unit therebetween;
   wherein the base unit, the stacking unit and the guard unit interconnect to provide a plurality of workstations and/or storage bays for a bioreactor.

As used herein, the term "biomolecule" can mean any molecule, such as a protein, peptide, nucleic acid, metabolite, chemical or biopharmaceutical that is produced by a cell.

In one aspect, the base unit and/or the stacking unit and/or the guard unit are movable.

In another aspect, the base unit and/or the stacking unit and/or the guard unit comprise wheels. In an embodiment, the wheels are reversibly lockable.

In a further aspect, the system further comprising a connection to utilities selected from the group consisting of electricity, water, nitrogen, oxygen, air and carbon dioxide. Optionally, the system further comprises a connection to a waste disposal outlet.

In an embodiment, the connections are reversibly connectable.

In one aspect, the system additionally comprises a connection to a refrigeration unit.

In another aspect, the platform within the base unit is movable in a vertical plane.

In a further aspect, the lower platform in the stacking unit is movable in a horizontal and/or a vertical plane.

In a further aspect, the platform in the guard unit is movable in a horizontal and/or a vertical plane.

In one aspect, the openable front wall of the guard unit is a sliding wall. It will be understood that the front wall may optionally be removable to provide user access to the unit.

In another aspect, the chamber of the base unit, the stacking unit and the guard unit comprise internal sterilizable surfaces to reduce the risk of contamination.

In a further aspect, the base unit, the stacking unit and the guard unit have a cuboid configuration.

In one aspect, the platform in the base unit and the stacking unit can support at least one bioreactor.

In another aspect, the bioreactor is a movement based bioreactor such as a WAVE bioreactor.

In a further aspect, the bioreactor is a stir tank bioreactor, such as an Xcellerex bioreactor.

In one aspect, the platforms are movable by electronic or pneumatic means.

In another aspect, the base unit and/or the guard unit are movable by electronic or pneumatic means.

In a further aspect, the system additionally comprises one or more bioreactor, such as a WAVE bioreactor.

According to a second aspect of the present invention, there is provided a use of a system as hereinbefore described as a workstation and/or a storage bay for a plurality of bioreactors.

In accordance with a third aspect of the present invention, there is provided a use of a system as hereinbefore described for cell culture and/or biomanufacturing.

According to a fourth aspect of the present invention, there is provided a method for cell culture comprising growing a cell culture in at least one bioreactor in a system as hereinbefore described to produce a plurality of cells.

In accordance with a fifth aspect of the present invention, there is provided a method for biomanufacturing comprising harvesting a biomolecule from a plurality of cells produced by the method of the fourth aspect.

According to a sixth aspect of the present invention, there is provide a system for cell culture and/or biomanufacturing comprising
  i. a housing comprising a plurality of vertically stacked workstations;
  ii. a mechanism for rotating said plurality of workstations; and
  iii. a port for providing user access to one of the workstations.

In accordance with a seventh aspect of the present invention, there is provided a use of a system according to the sixth aspect as a workstation and/or a storage bay for a plurality of bioreactors.

According to an eighth aspect of the present invention, there is provided a use of a system according to the sixth aspect for cell culture and/or biomanufacturing.

In accordance with a ninth aspect of the present invention, there is provided a method for cell culture comprising growing a cell culture in at least one bioreactor in a system according to the sixth aspect to produce a plurality of cells.

According to a tenth aspect of the present invention, there is provided a method for biomanufacturing comprising harvesting a biomolecule from a plurality of cells produced by the method of the ninth aspect.

BRIEF DESCRIPTION OF THE FIGURES

The features and advantages of the invention will become apparent from the following description taken in connection with the accompanying drawings in which.

DETAILED DESCRIPTION OF THE INVENTION

Figure 1:
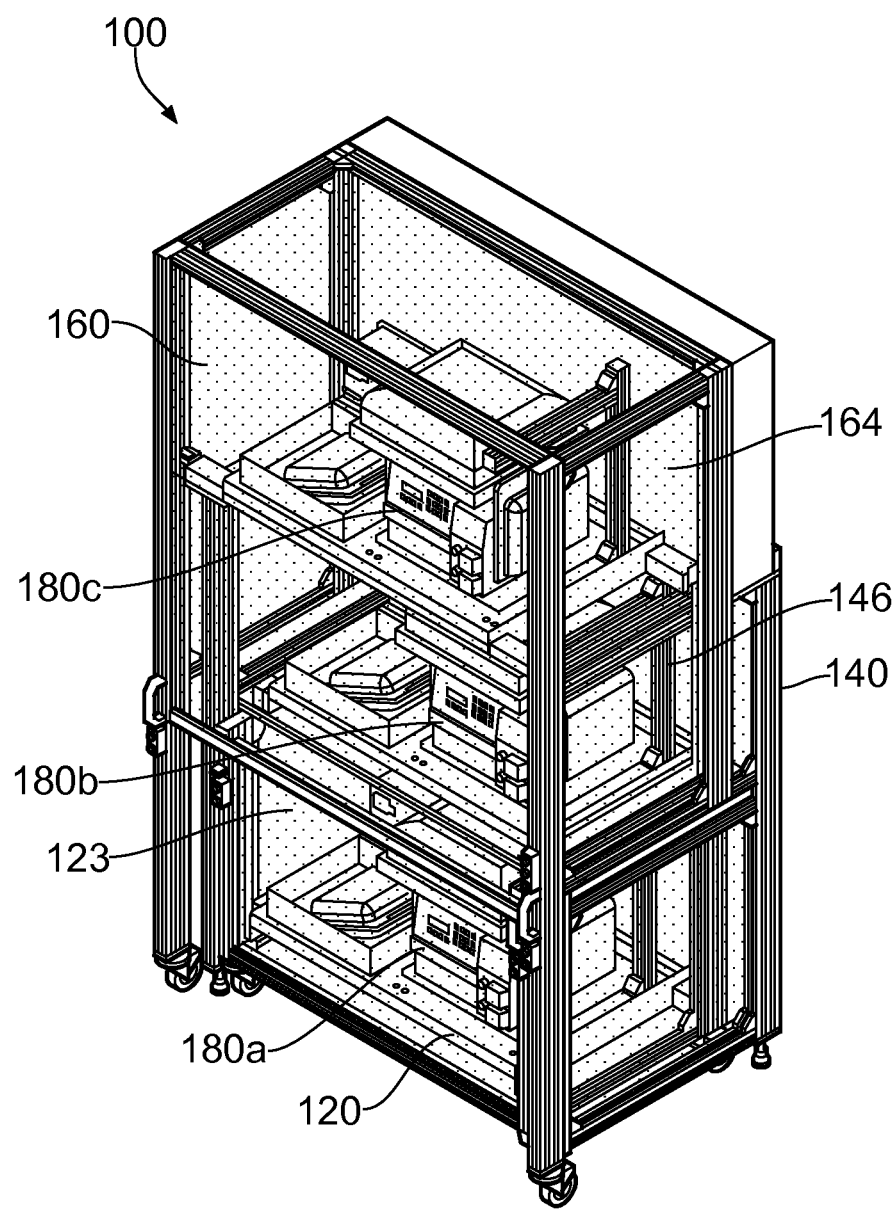
FIG. 1 depicts a perspective view of one embodiment of a system according to the invention housing or storing a plurality of bioreactors.

Embodiments of the present invention relate to a system for cell culture and/or biomanufacturing. In particular, embodiments of the present invention relate to a system for providing a plurality of workstations and/or storage bays for bioreactors. FIG. 1 is a schematic perspective view of a system 100 in accordance with an embodiment of the invention. The system 100 consists of a base unit 120, a stacking unit 140 and a guard unit 160. The system 100 shown in FIG. 1 is in a resting or storage position or configuration and is shown in use housing or storing bioreactors (e.g. 180a, b, c) in a series of chambers (123, 146, 164) or storage bays.

Figure 2:
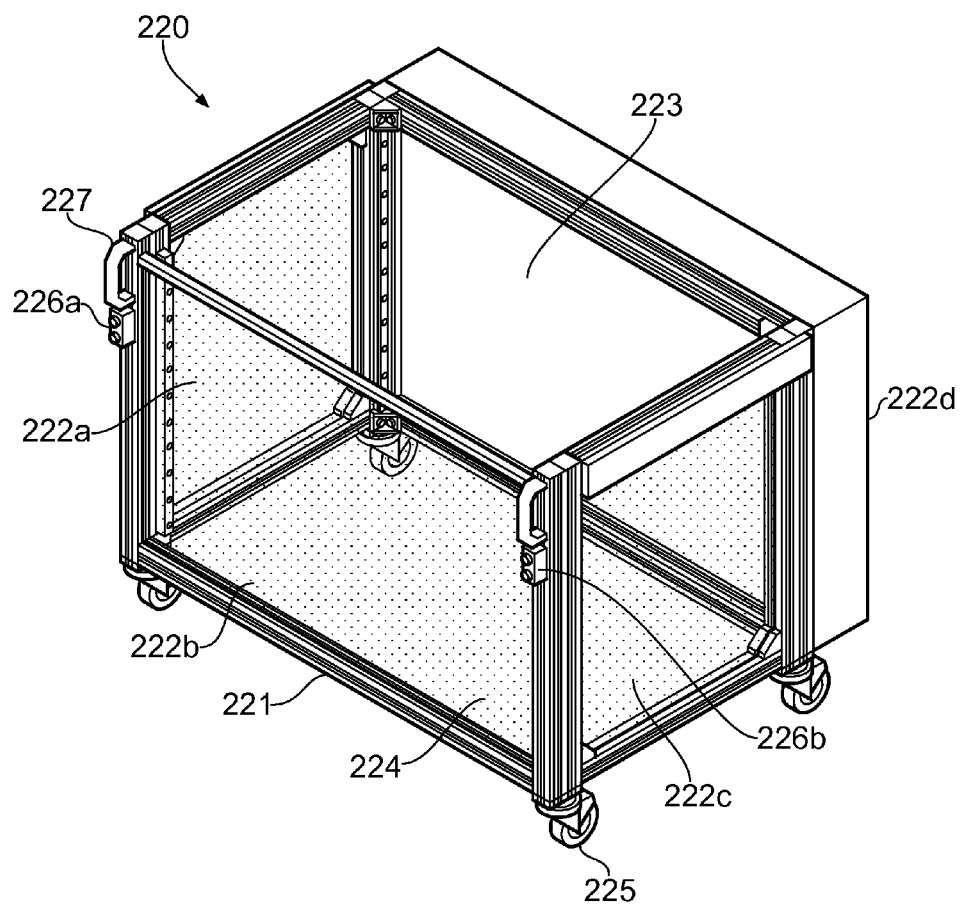
FIG. 2 illustrates a perspective view of a base unit of the system of FIG. 1 (but does not show the bioreactor)

FIG. 2 shows a schematic perspective view of a base unit 220 of the system in accordance with an embodiment of the invention. The base unit 220 consists of a frame 221 supporting walls (222a, b, c, d) and a movable platform 224 which forms a base and thereby defines a chamber 223 within the unit. One of the walls 222d may optionally be reinforced and act as a spacer and/or support when the system is in a closed or storage configuration (FIG. 1). The movable platform 224 is designed to provide a support for a bioreactor (not shown in the figure). Control panels (226 a,b) may be used to automatically raise or lower the movable platform 224 within the base unit 220. The base unit 220 may also have wheels (e.g. 225) or coasters or be on a trolley or rail system to facilitate movement of the base unit into and out of the system 100 and so provide user access to the interior chamber 223 of the unit. The interior chamber 223 may also serve as a storage bay for one or more bioreactors. Handles (e.g. 227) may be provided to assist the user in moving the base unit 220. The wheels (e.g. 220) may optionally be reversibly lockable to increase the stability of the unit 220.

Figure 3:
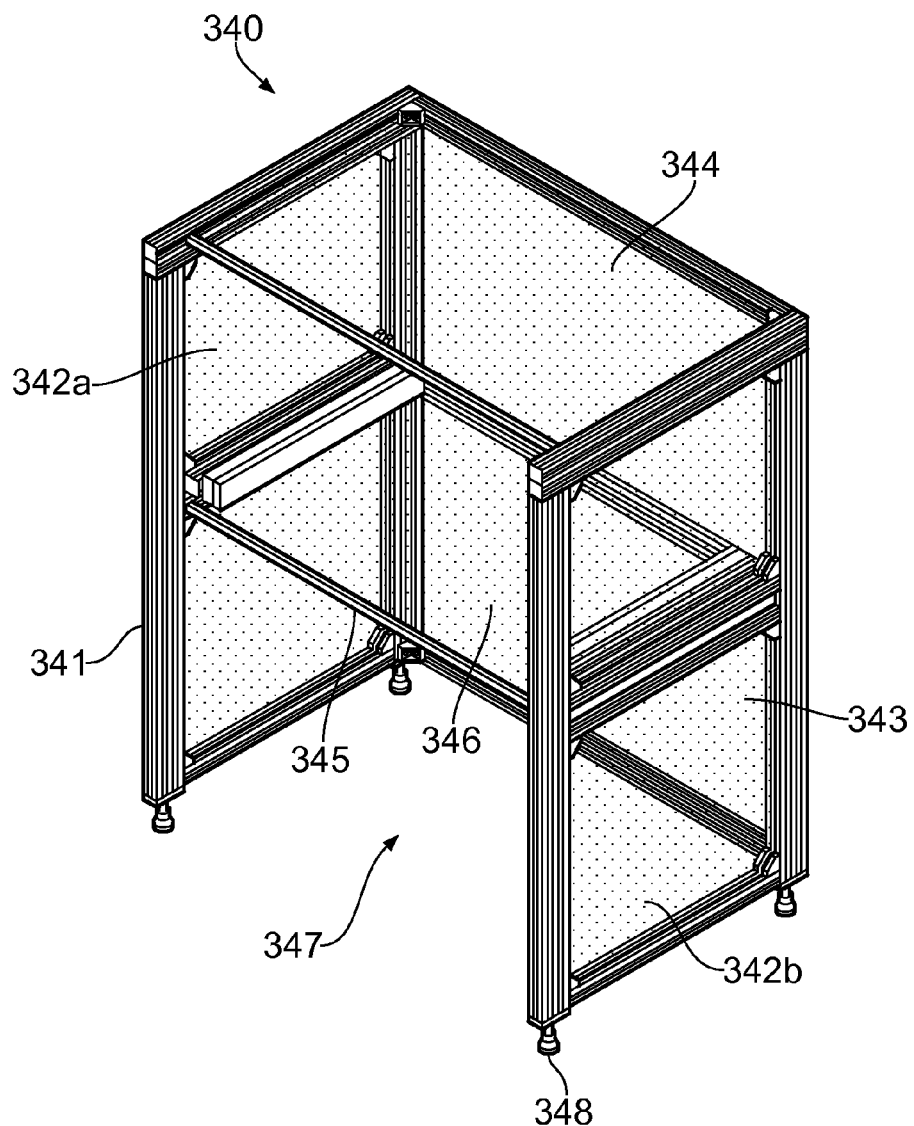
FIG. 3 shows a perspective view of a stacking unit of the system of FIG. 1 (but does not show the bioreactor)

FIG. 3 is a schematic perspective view of a stacking unit 340 of a system in accordance with an embodiment of the invention. The stacking unit 340 consists of a frame 341 supporting side walls 342 a, b, an optional back wall 343, a ceiling or roof 344 and a movable platform 345 which define an upper 346 and a lower 347 chamber. The lower chamber 347 is dimensioned such that it can receive the base unit (FIG. 2) within it. The platform 345 is designed to provide a support for a bioreactor (not shown) within the upper chamber 346 which may also serve as a storage bay for a bioreactor. The base of the frame 341 may optionally have feet (e.g. 348) to provide stability for the unit. In other embodiments, the frame 341 may have lockable wheels rather than feet 348 to provide mobility and stability. In yet other embodiments, the stackable unit 340 may be secured into place, for example by bolting against a wall and/or to the floor to provide stability.

Figure 4:
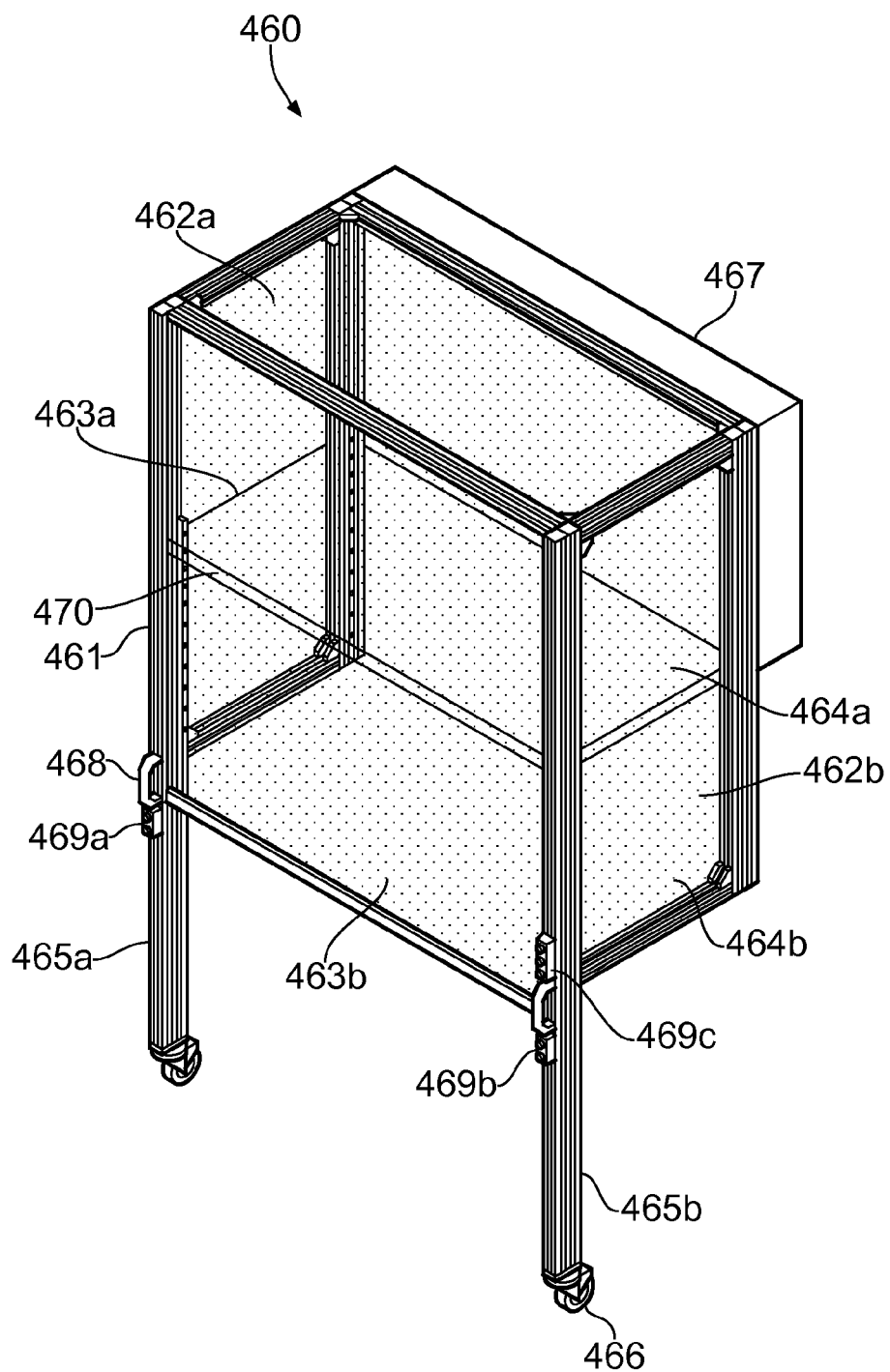
FIG. 4 presents a perspective view of a guard unit of the system of FIG. 1 (but does not show the movable platform supporting the bioreactor)

FIG. 4 is a schematic perspective view of a guard unit 460 of a system in accordance with an embodiment of the invention. The guard unit 460 consists of a frame 461 supporting side walls 462a, b, an openable front wall 463 a,b, and a movable platform 470 which define an upper chamber 464a and a lower chamber 464b which is dimensioned to partially receive the stacking unit (FIG. 3). The guard unit 460 is supported on legs 465 a,b which may also have wheels (e.g. 446) or coasters or be on a trolley or rail system to facilitate movement of the guard unit away from the base unit 120 and stacking unit 140 (FIG. 1) and provide user access to the interior of chamber 464. Handles 468 are provided to assist the user in moving the guard unit 460 away from/towards the base unit 120 and stacking unit 140. As shown in the figure, optionally there may be a rear wall 467 opposing wall 463 which may be reinforced to act as a spacer and/or support when the system is in a closed or storage configuration (FIG. 1). In the embodiment shown, the interior chamber 464 is accessible via the openable wall 463a,b by means of sliding panel 463b, The movable platform 470 is used to support a bioreactor, as seen in FIG. 1. Control panels 469 a,b,c are used to raise and/or lower the movable platform 470.

In embodiments of the invention, movable platform 470 is replaced with a movable ceiling or roof of the stacking unit.

Figure 5:
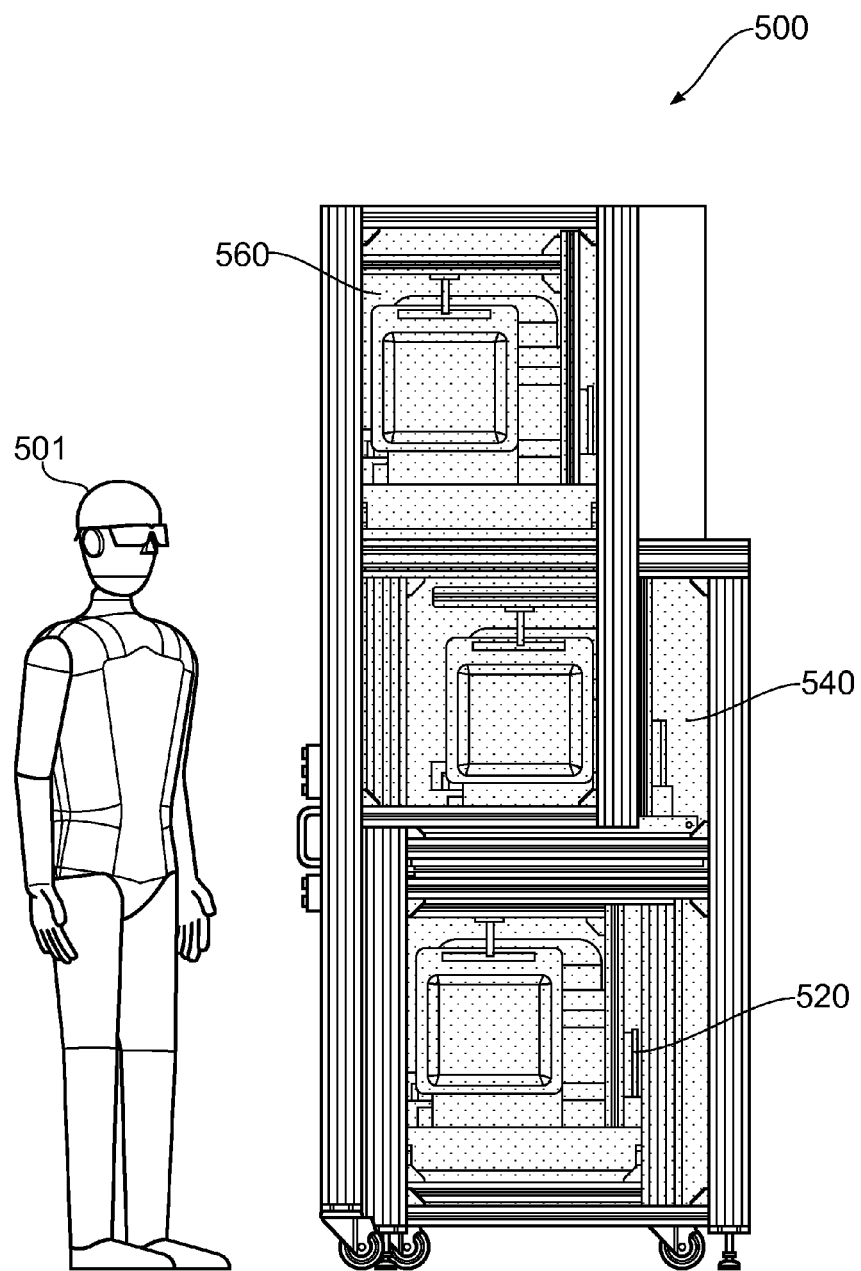
FIG. 5 illustrates a side view of the system of FIG. 1.

FIG. 5 is a side view of the system 500 of FIG. 1. For illustrative purposes, a schematic user 501 is shown facing the front of the system 500. As with FIG. 1, the system 500 is shown in a closed or storage configuration housing or storing bioreactors. The component parts of the system 500 can be seen to be the base unit 52, the stacking unit 540 and the guard unit 560. From this perspective, it can be seen that the base unit 520 is accommodated within the lower chamber of the stacking unit 540 which is itself partially surrounded by or received within the chamber of the guard unit 560.

Use of the system of embodiments of the invention as depicted in FIGS. 1 to 5 will be described with reference to FIGS. 6 to 19 below. It is expected that the system will be maintained in a clean area such as a tissue culture suite or biomanufacturing facility to minimise the risk of microbial contamination. Bioreactors will be housed or stored in the system until such time as it is necessary to carry out work on them and the growing cultures, such as sub-culturing or harvesting cells, media and/or biomolecules.

Figure 6:
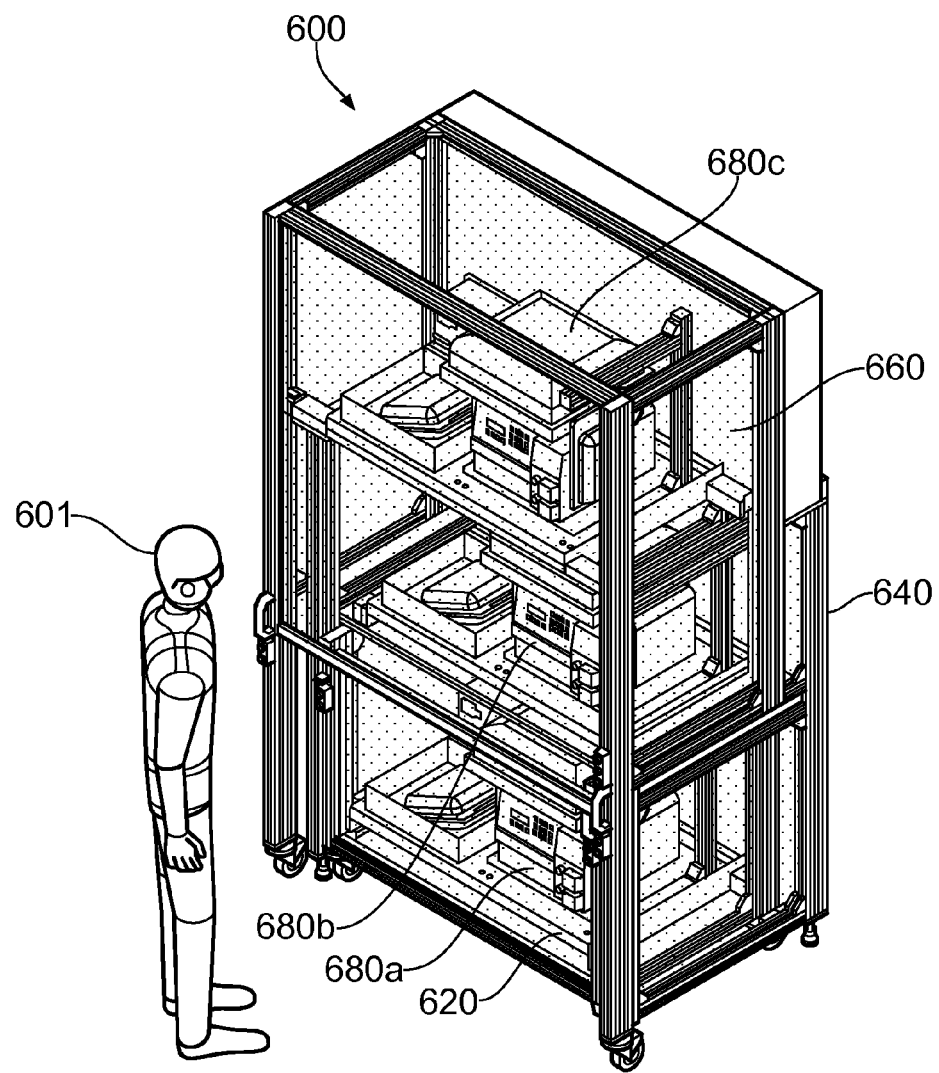
FIG. 6 provides another perspective view of one embodiment of a system according to the invention housing or storing a series of bioreactors.

FIG. 6 is a schematic perspective view of a system 600 in accordance with an embodiment of the invention as shown in FIG. 1. For illustrative purposes a user 601 in depicted in front of the system 600 which comprises a base unit 620, a stacking unit 640 and a guard unit 660. Again for illustrative purposes, the system 600 is shown housing or storing bioreactors 680a, b, c. in a closed or storage configuration. It will be understood, that while the embodiment shown houses or stores one bioreactor 680 in each of the three units (620, 640 and 660), other embodiments of the system are capable of storing or housing more than one bioreactor in each unit; thus, for example, the system can house or store a total of six, or nine, or twelve, or more bioreactors depending upon the size of the respective units.

To use the system 600 the user, in the interests of safety, would first turn off and disconnect the supply of utilities (such as electricity, water, nitrogen, oxygen, air and carbon dioxide) to the system. The user may also disconnect any waste removal or outlet conduits from the system.

Figure 7:
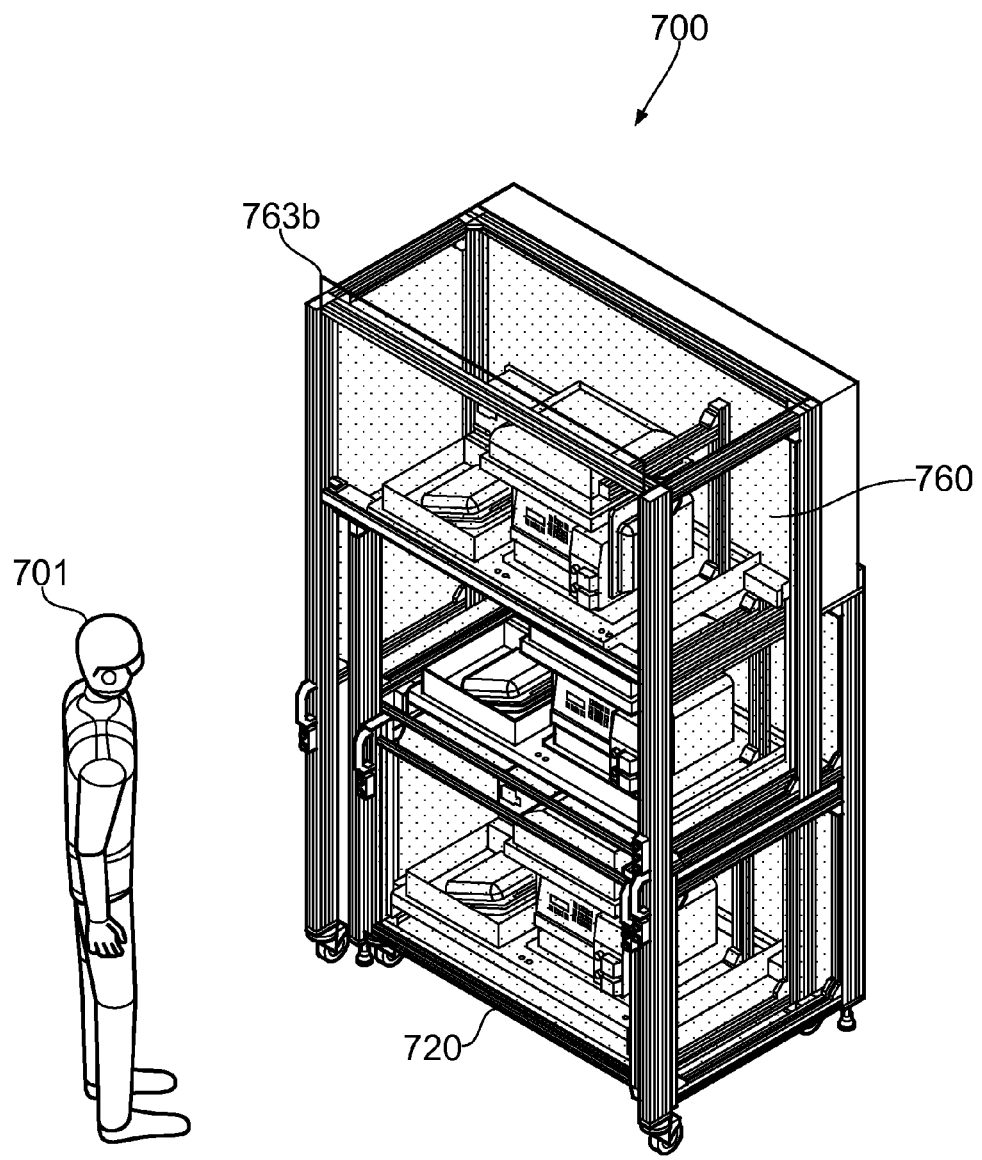
FIG. 7 illustrates a perspective view of the system of FIG. 1 or 6 in which the front wall of the guard unit is in an open configuration to allow user access to the base unit.
Figure 8:
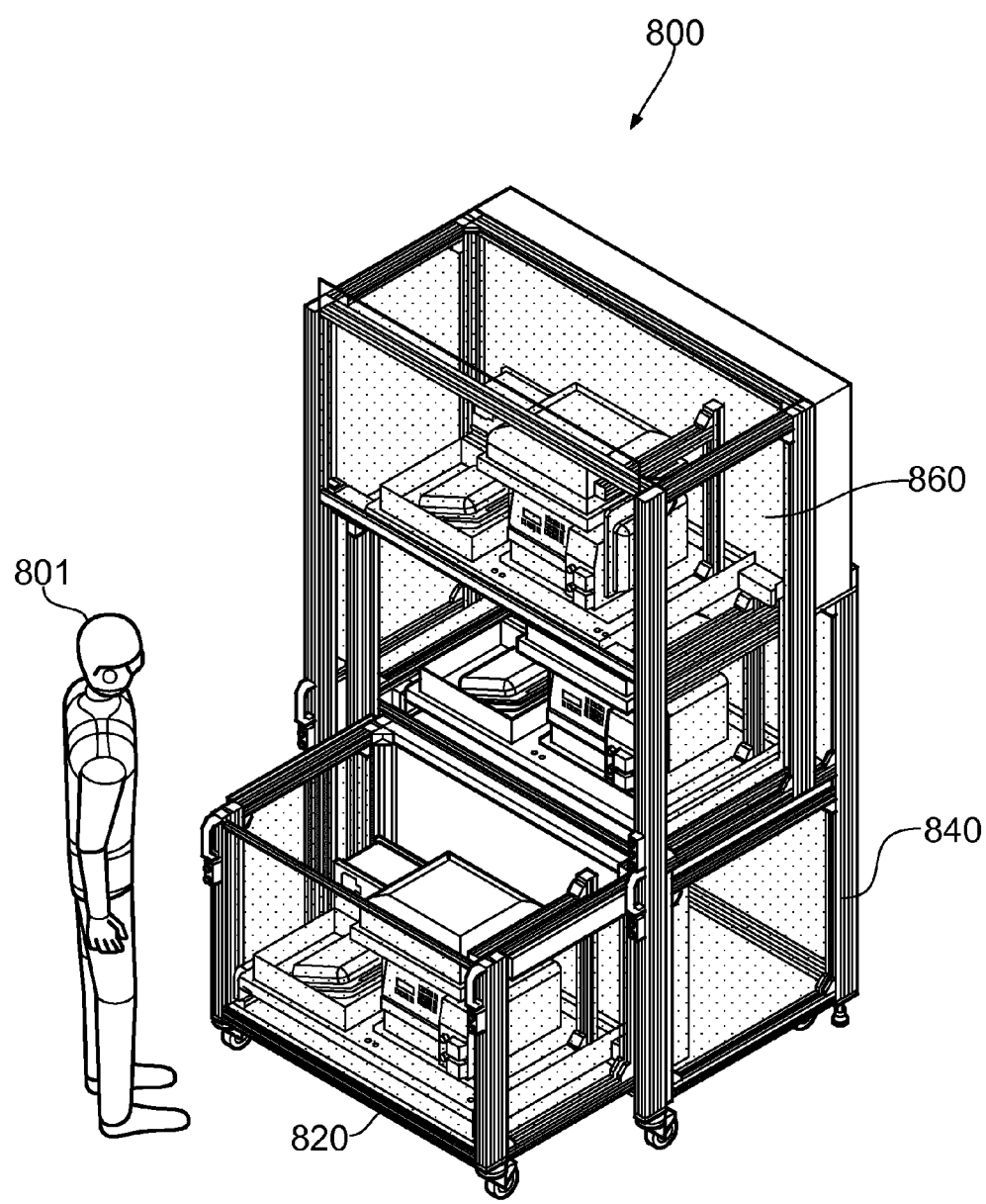
FIG. 8 shows a perspective view of the system of FIG. 7 in which the base unit has been moved away from the lower chamber of the stacking unit.
Figure 9:
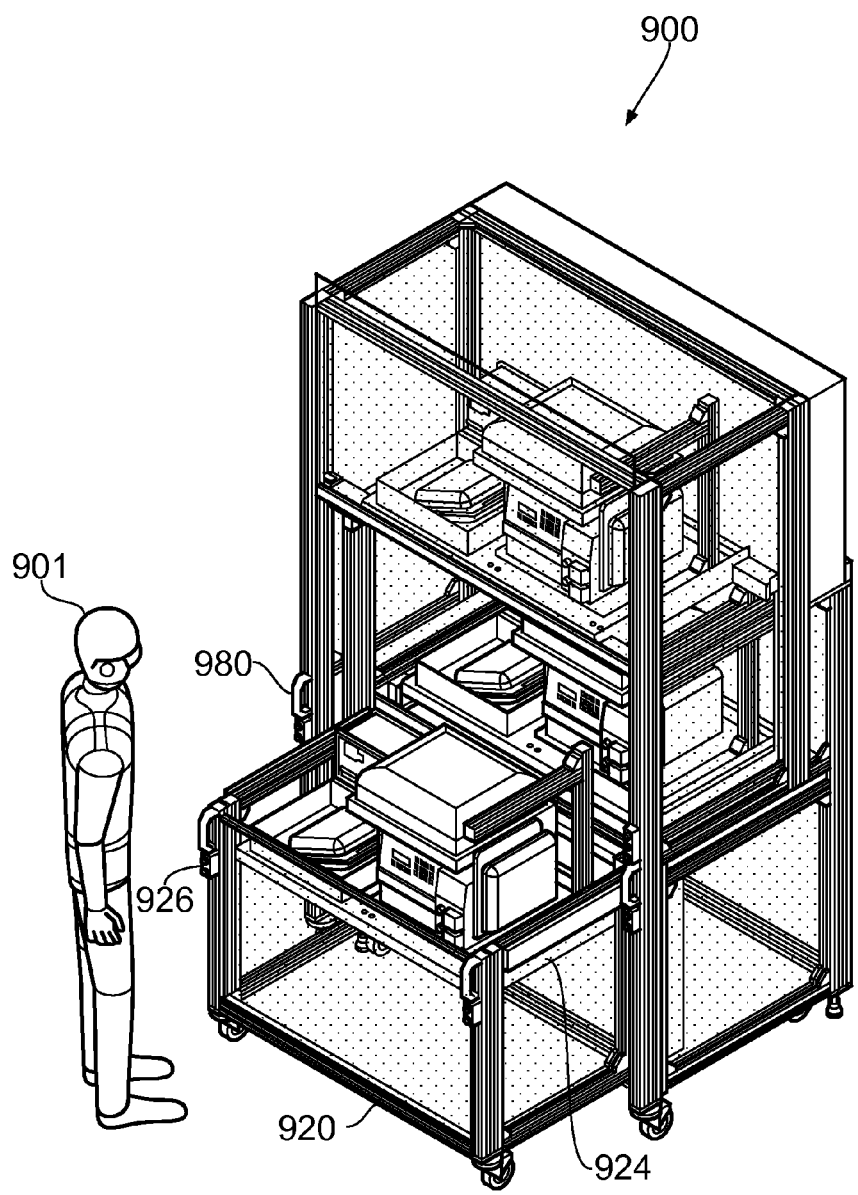
FIG. 9 depicts a perspective view of the system of FIG. 8 in which the movable platform within the base unit has been raised to provide user access to the bioreactor housed or stored within the chamber.
Figure 10:
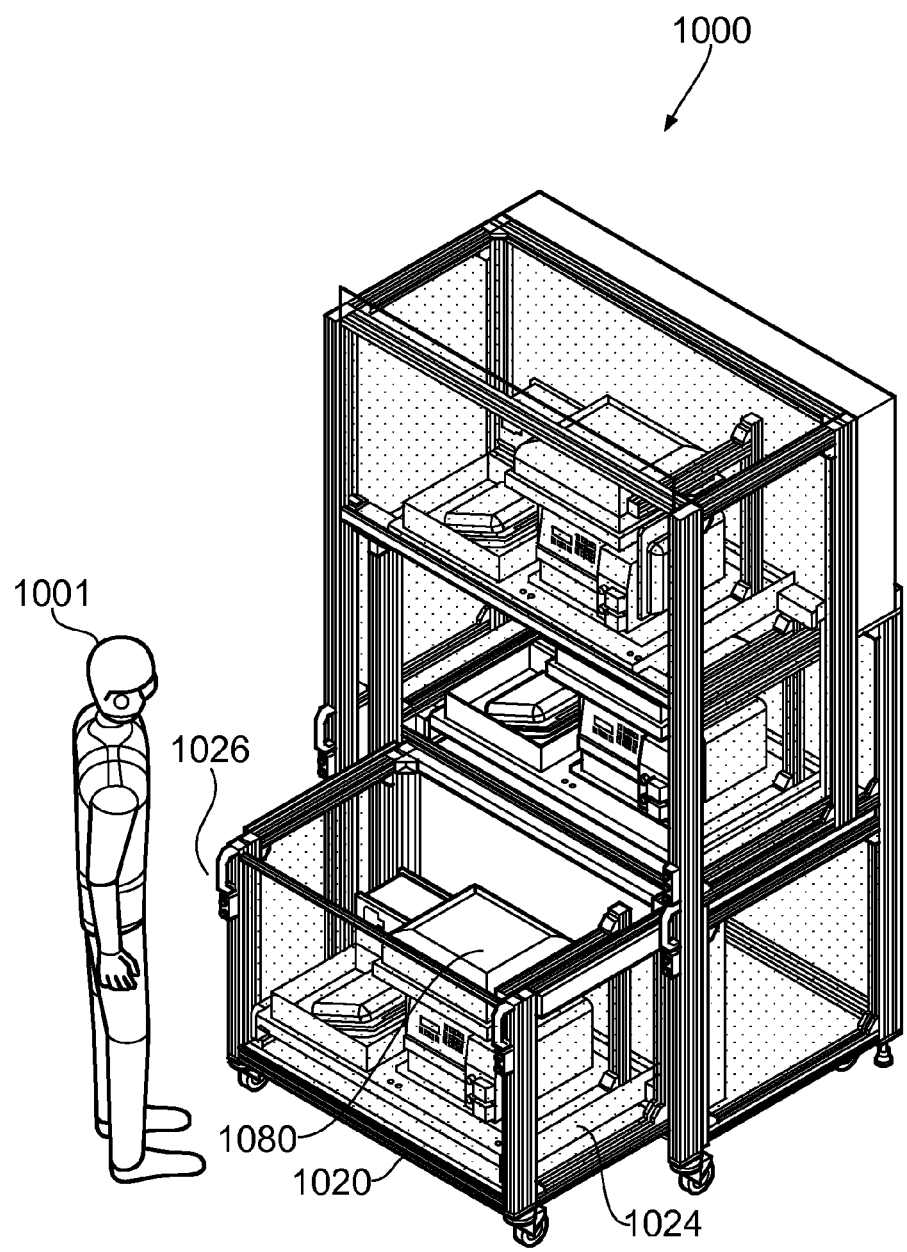
FIG. 10 depicts a perspective view of the system of FIG. 9 in which the movable platform of the base unit has been lowered to return the bioreactor to a housing or storage position.
Figure 11:
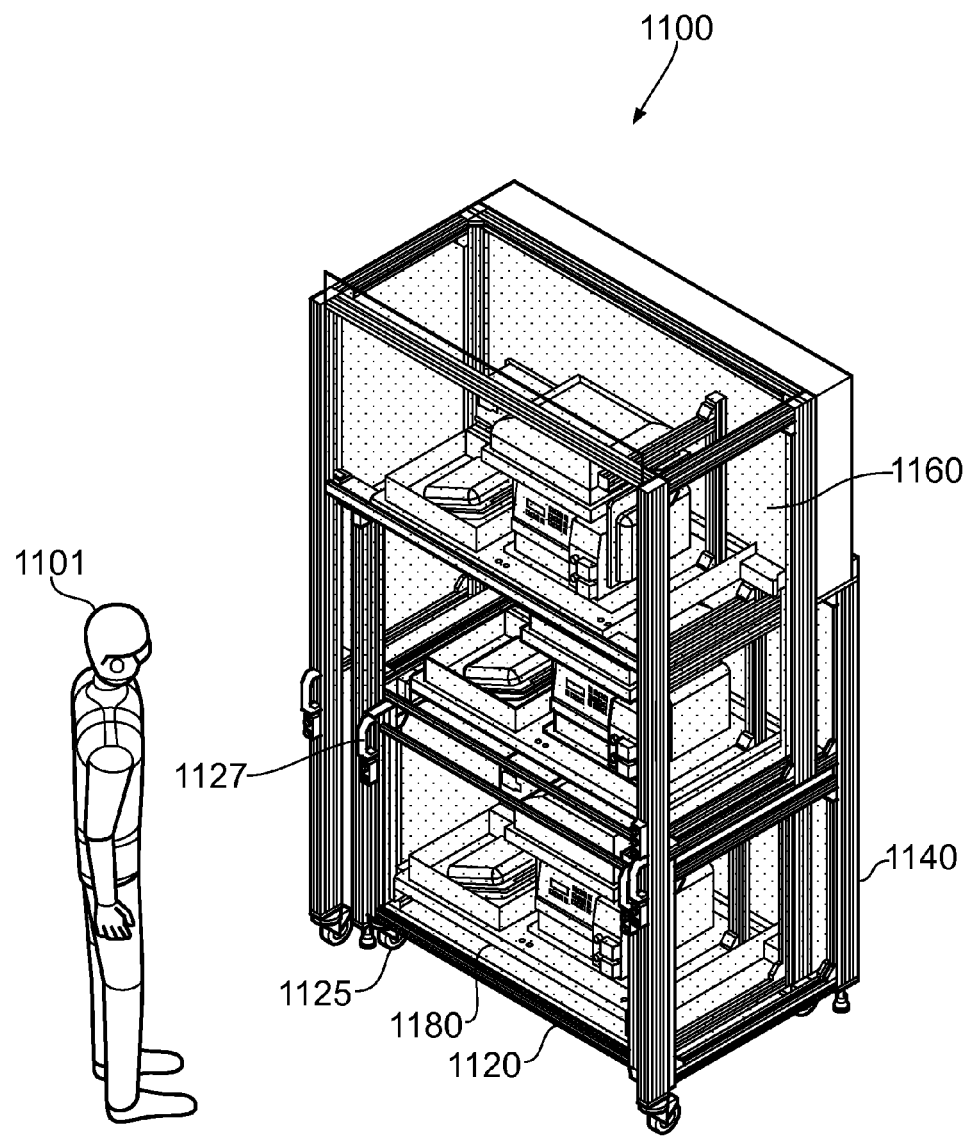
FIG. 11 shows a perspective view of the system of FIG. 10 in which the base unit has been moved back or returned to the lower chamber of the stacking unit.

The user can then open the sliding panel 763b of the guard unit 760 which provides the user 701 access to the base unit 720 (FIG. 7). The base unit 820 can then be pulled or moved away from the stacking unit 840 and guard unit 860 (FIG. 8). The user 901 would then raise the movable platform 924 supporting the bioreactor 980 by means of the control panel 926 to provide a workstation which is at a convenient height and is easily accessible. Work, such as culture maintenance or harvesting, can now be carried out on the cultures within the bioreactor 980 (FIG. 9). Once work has been completed on the bioreactor 1080 and/or the cultures therein, the user 1001 lowers the movable platform 1024 by means of the control panel 1026 (FIG. 10). The user 1101 now pushes the base unit 1120 back into position, utilising handles 1127, within the stacking unit 1140 and guard unit of the system 1100 (FIG. 11). The bioreactor 1180 is now in its resting or storage position within the base unit 1120 of the system 1100 and the wheels 1125 of the base unit 1120 locked to secure it in position.

Figure 12:
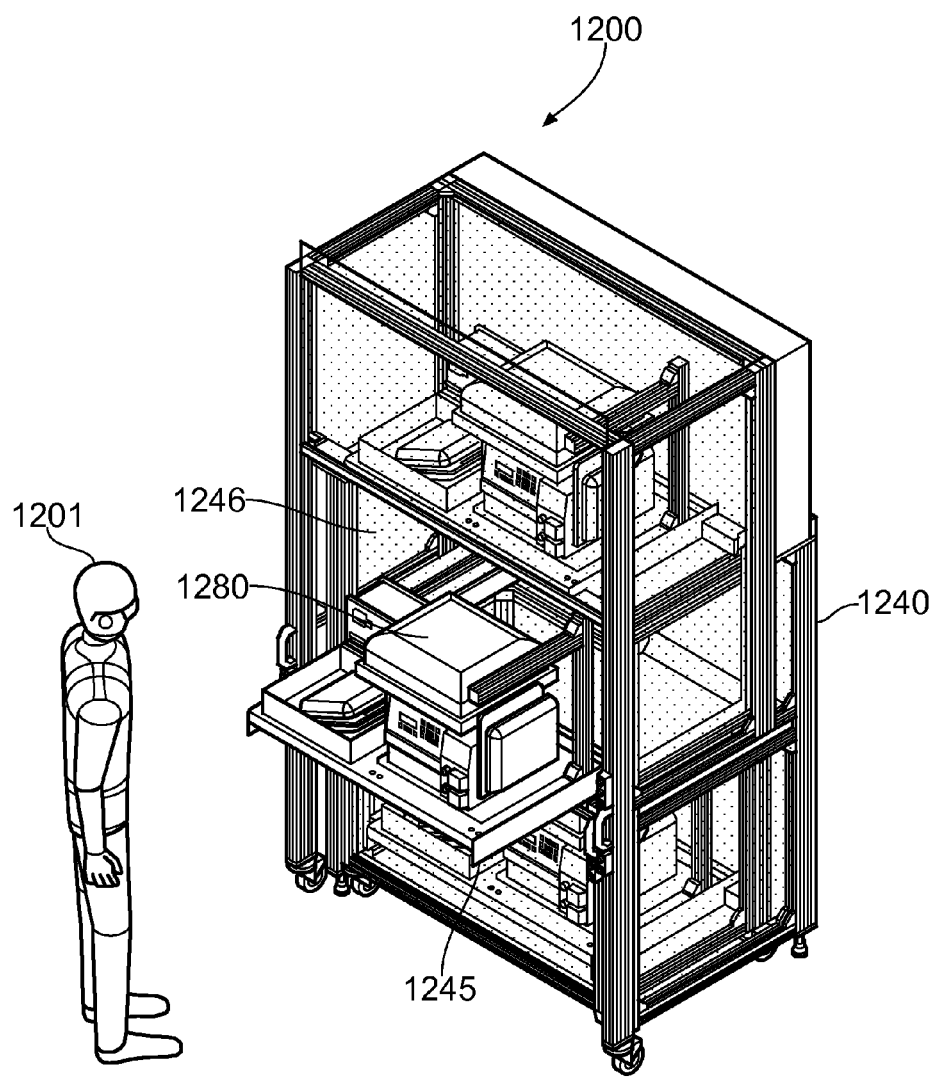
FIG. 12 is a perspective view of the system of FIG. 11 in which the lower platform of the stacking unit has been moved or pulled out from the stacking unit to allow user access to the bioreactor.
Figure 13:
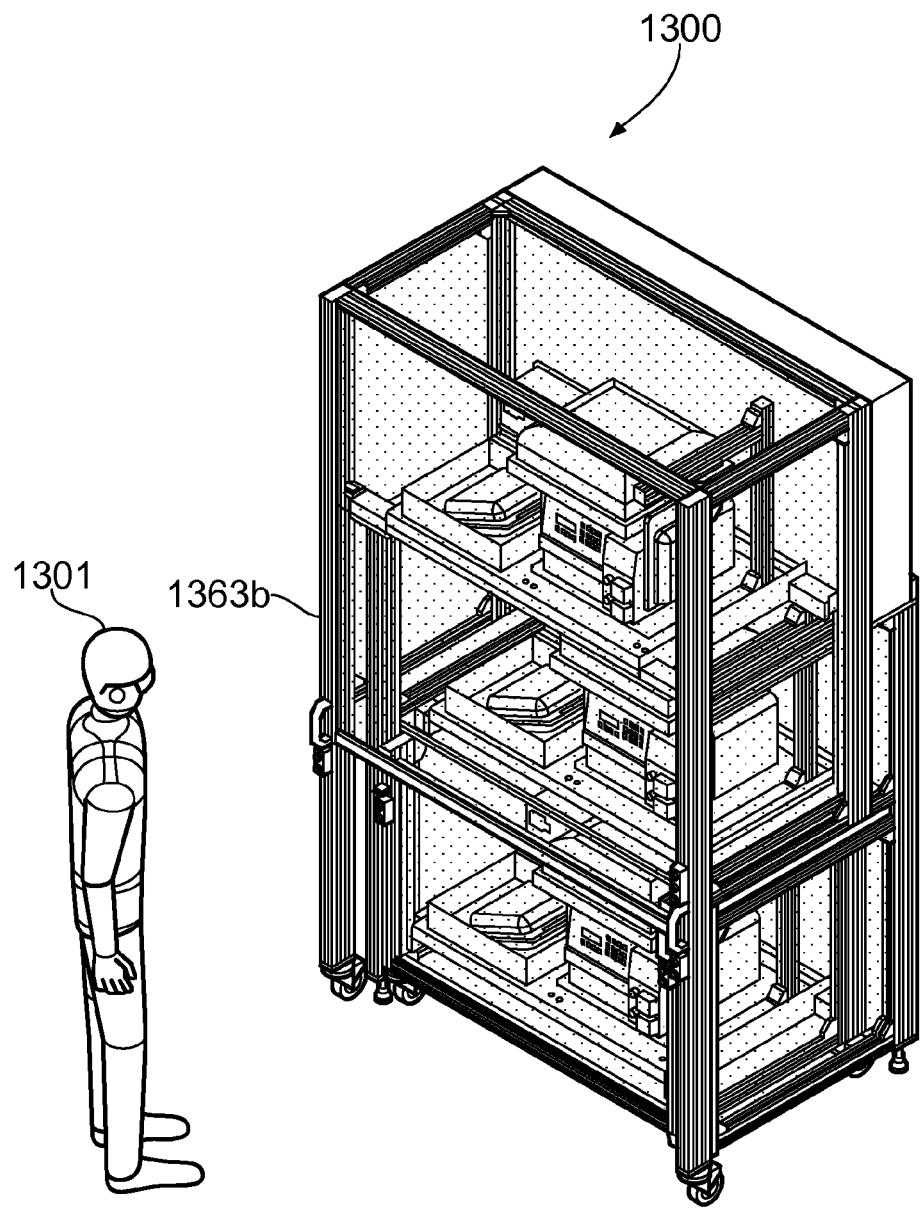
FIG. 13 depicts a perspective view of the system of FIG. 12 in which the lower platform of the stacking unit has been moved or returned to the stacking unit and the wall of the guard unit closed.

To work on the bioreactor 1280 within the stacking unit 1240, the user 1201 pulls the movable platform 1245 from the upper chamber 1246 of the stacking unit 1240 (FIG. 12). This creates a work station for the user 1201 who can now readily access the bioreactor 1280. Maintenance work, such as sub-culturing, cell harvesting or biomolecule harvesting, can now be carried out on the cultures within the bioreactor 1280. Once work has been completed the platform 1245 is pushed back into chamber 1246 of the stacking unit 1240 (FIG. 12) and the sliding panel 1363b is closed to return the system 1300 into its resting or storage position (FIG. 13).

Figure 14:
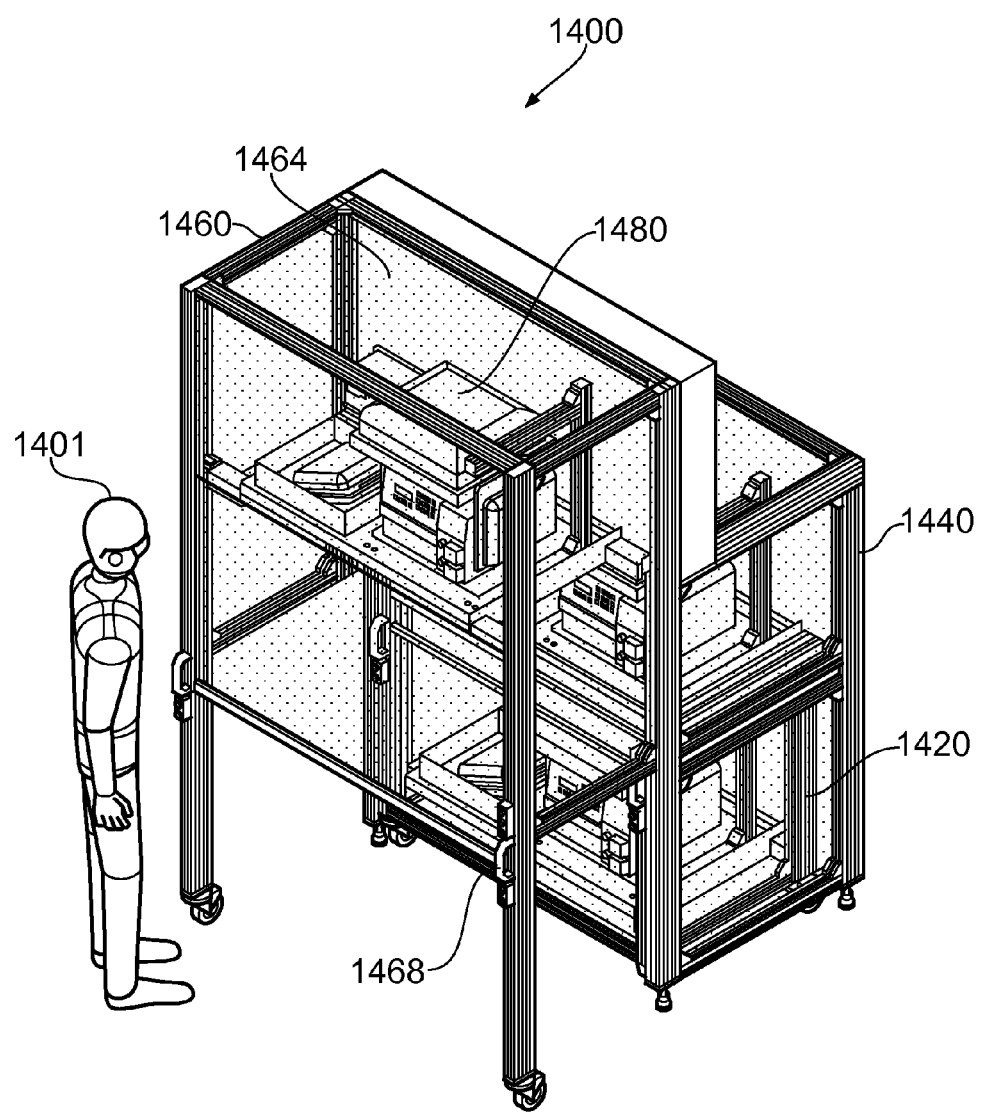
FIG. 14 shows a perspective view of the system of FIG. 13 in which the guard unit housing or storing a bioreactor has been moved or pulled away from the base unit and the stacking unit.
Figure 15:
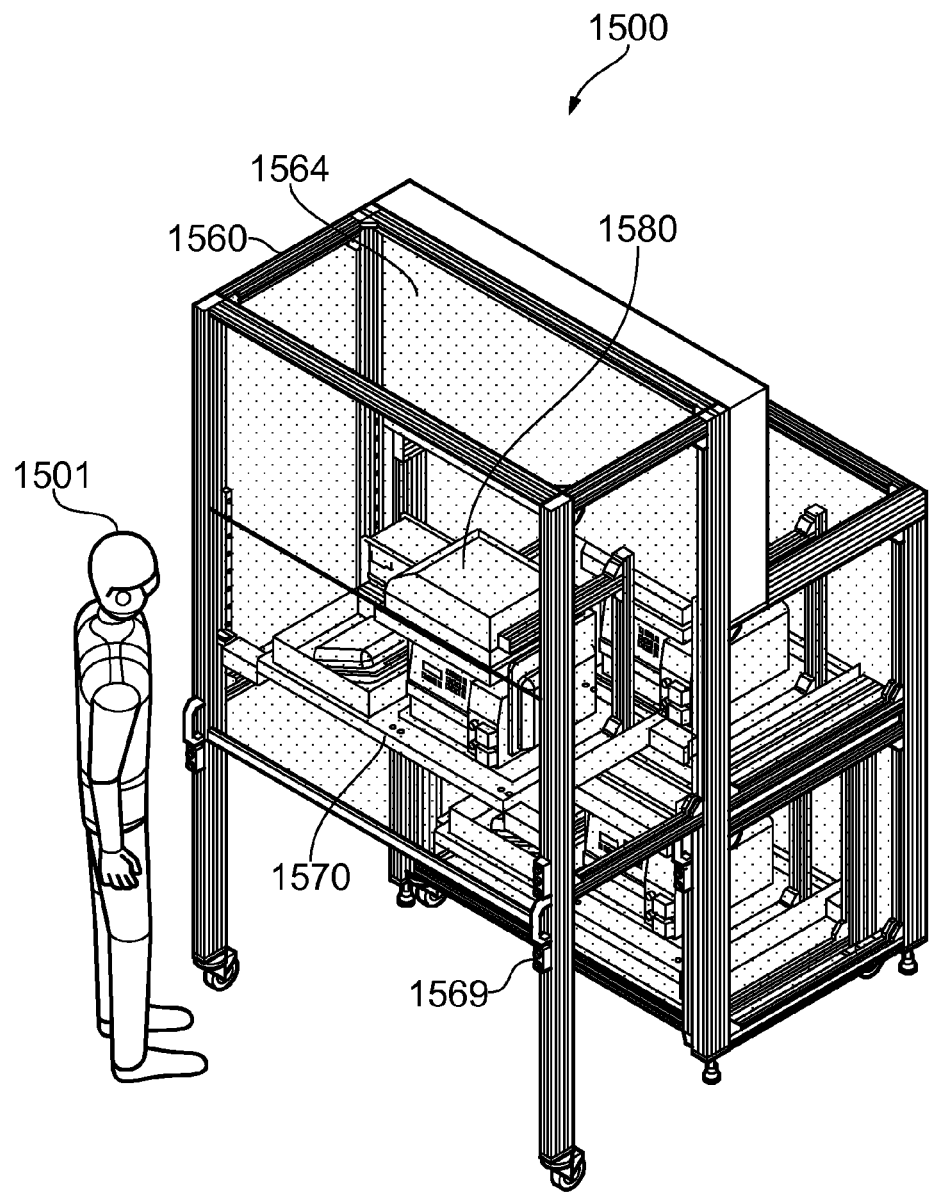
FIG. 15 illustrates a perspective view of the system of FIG. 14 in which the movable platform of the guard unit supporting a bioreactor has been lowered.
Figure 16:
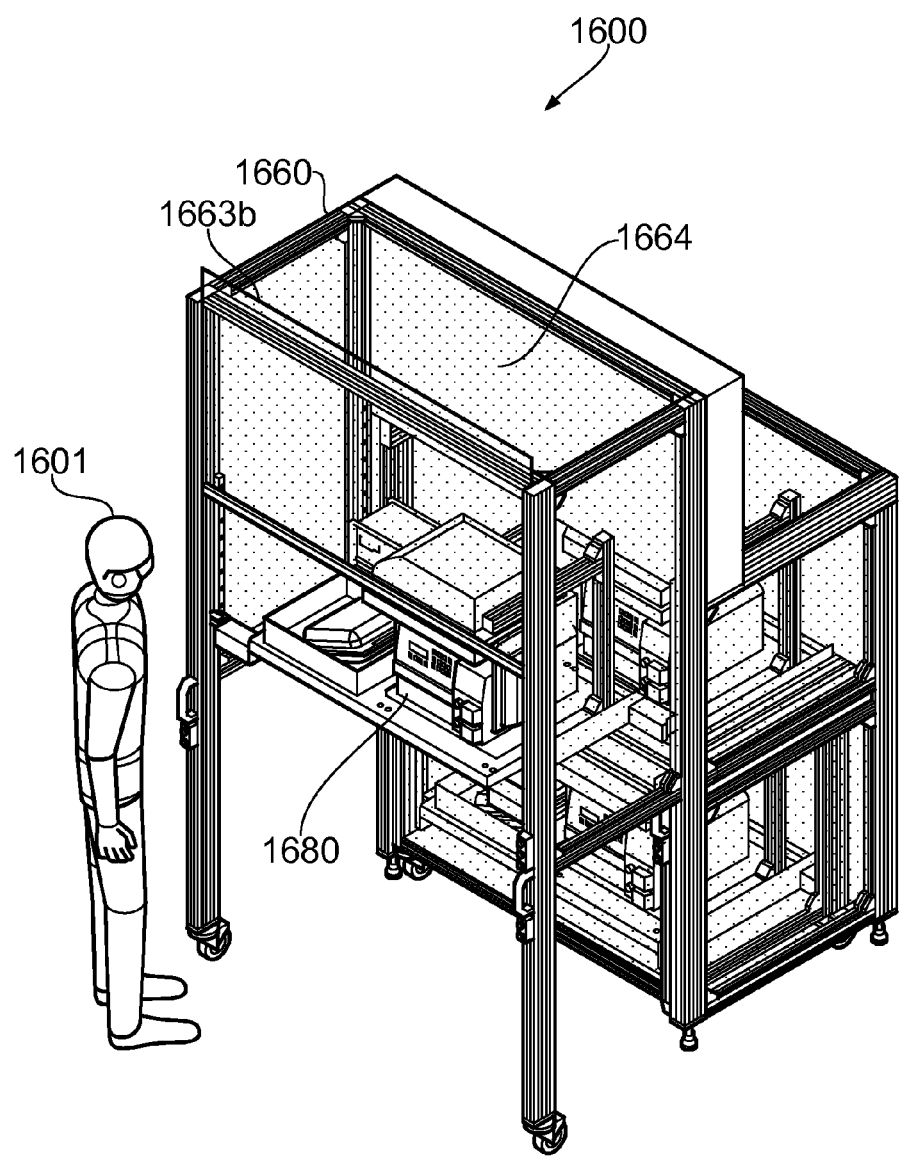
FIG. 16 depicts a perspective view of the system of FIG. 15 in which the front wall of the guard unit is in an open configuration to allow user access to the bioreactor.
Figure 17:
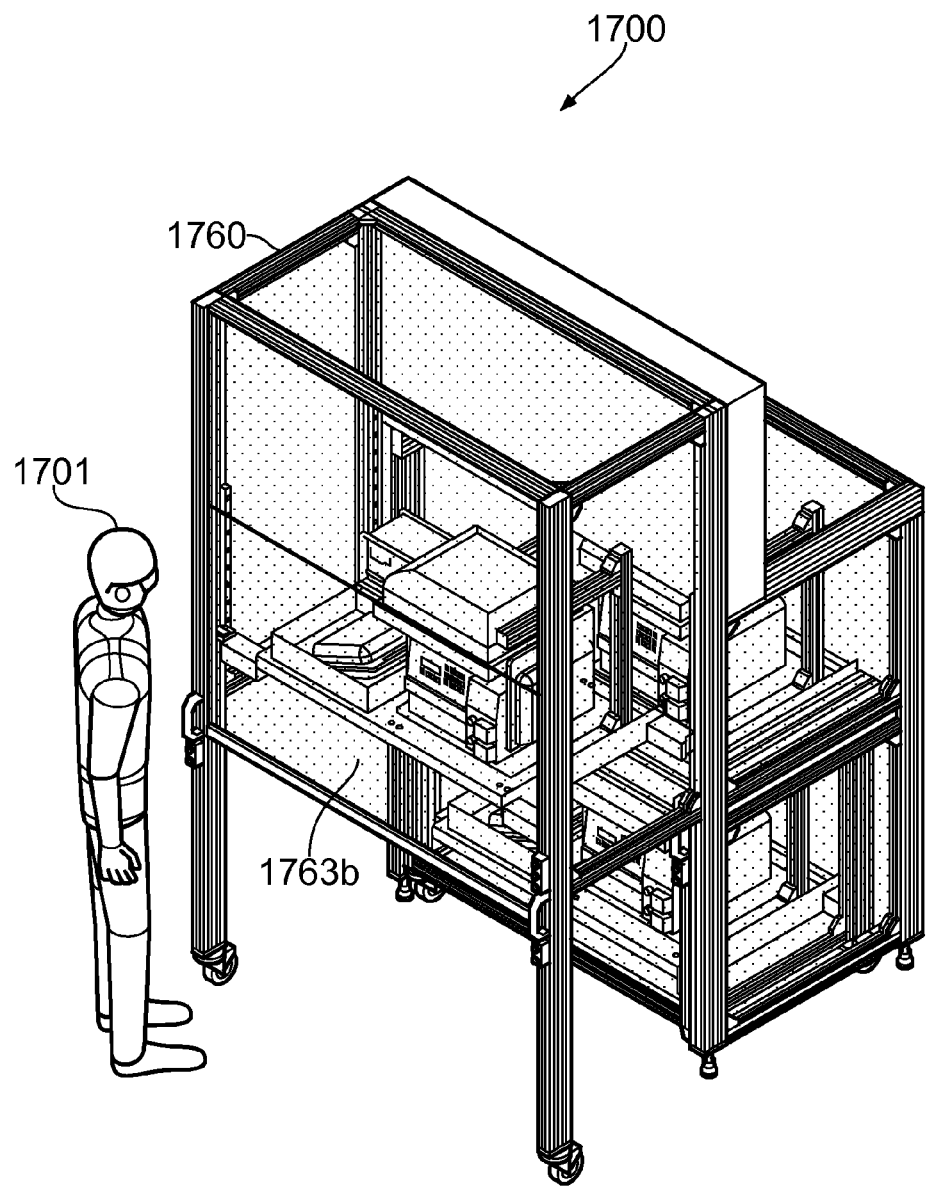
FIG. 17 is a perspective view of the system of FIG. 16 in which the front wall of the guard unit is in a closed configuration.
Figure 18:
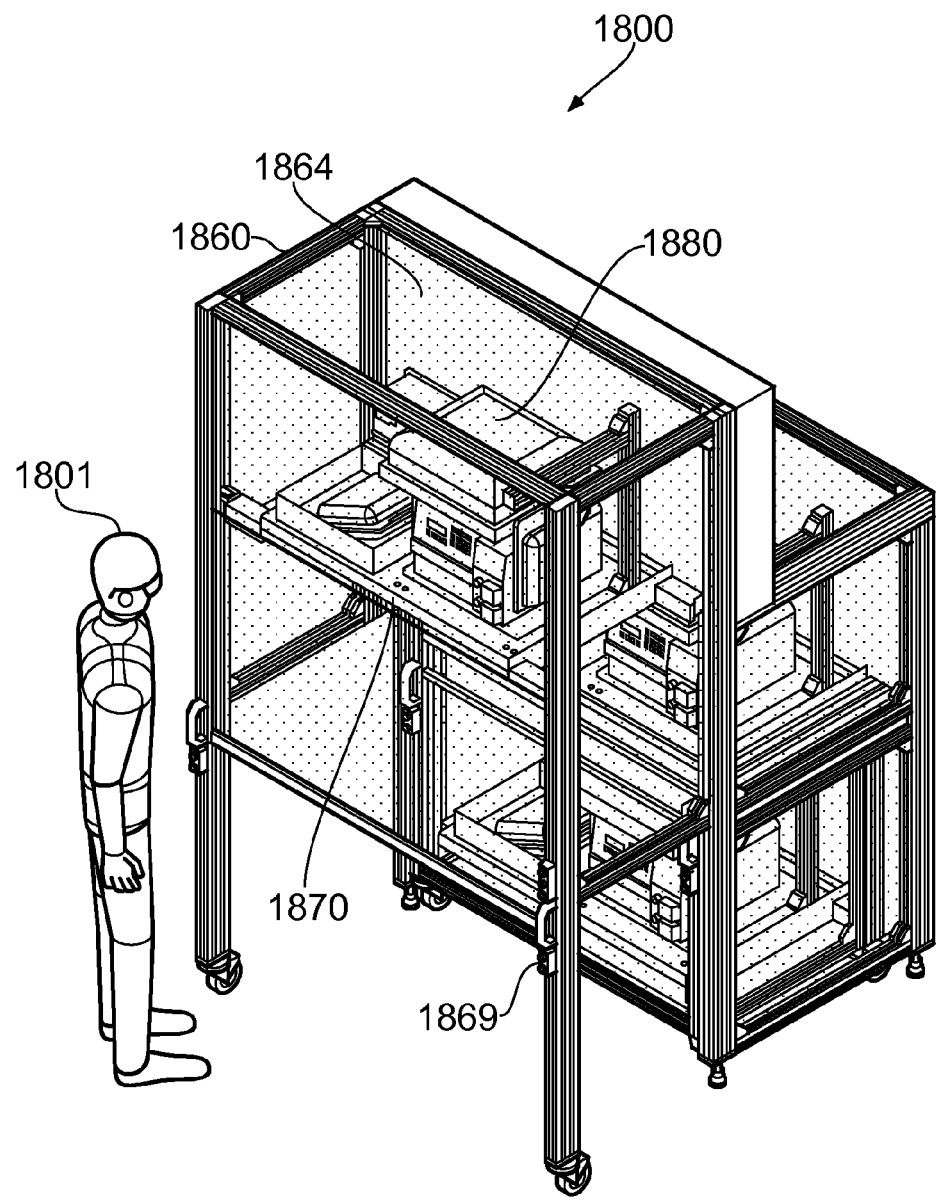
FIG. 18 provides a perspective view of the system of FIG. 17 in which the movable platform of the guard unit has been raised.
Figure 19:
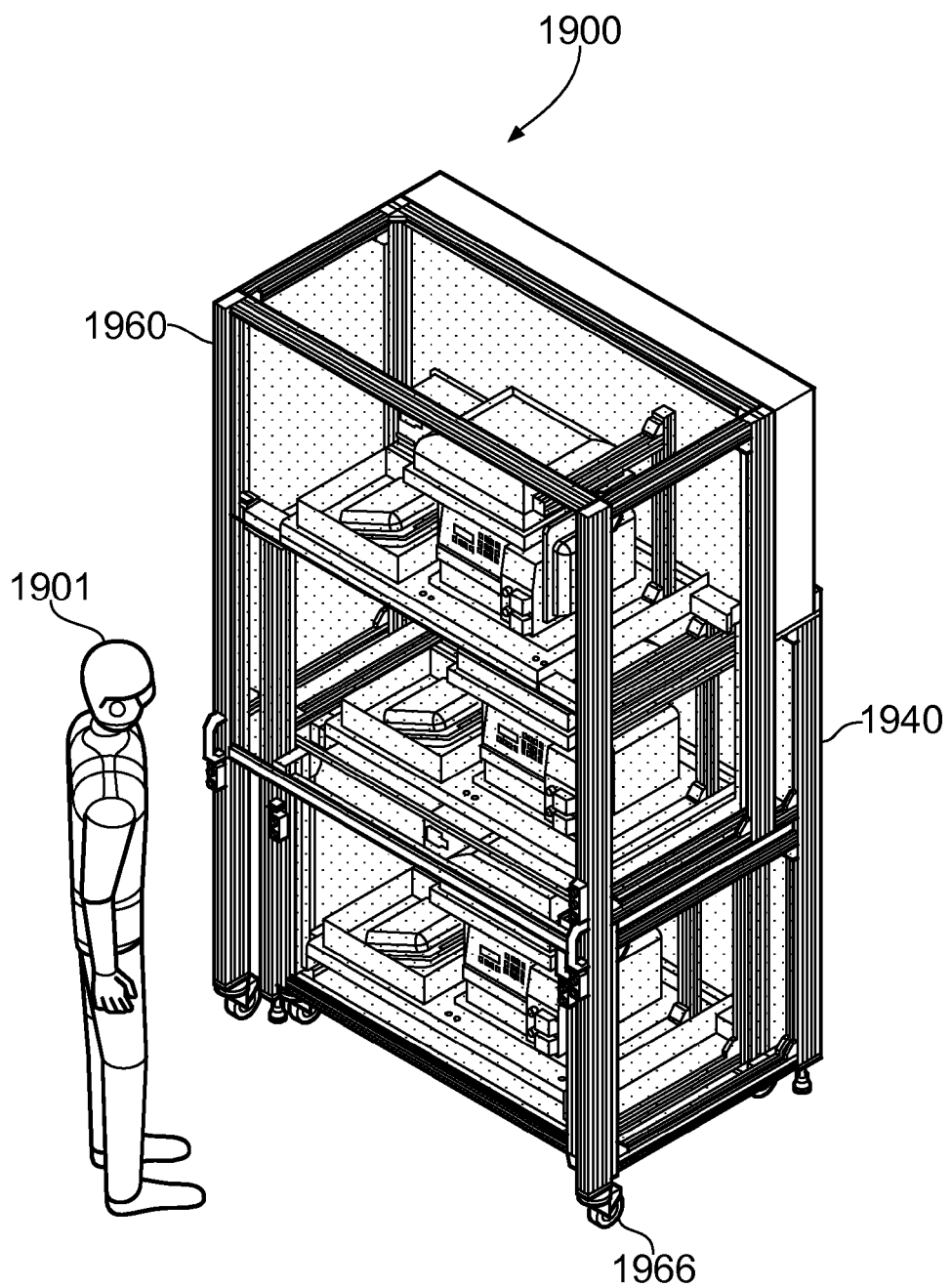
FIG. 19 is a perspective view of the system of FIG. 18 in which the guard unit has been moved back into position to enclose the stacking unit.

To access the bioreactor 1480 in the chamber 1464 of guard unit 1460 in system 1400, the user 1401 first pulls the guard unit 1460 away from the stacking unit 1440 using handles 1468 as shown in FIG. 14. The movable platform 1570 supporting the bioreactor 1580 in the chamber 1564 is lowered by means of the control panel 1569 to user 1501 level (FIG. 15). The sliding panel 1663b may then be opened to provide user 1601 access to the bioreactor 1680 within the chamber 1664 of the guard unit 1660 (FIG. 16) and thus a workstation. The user 1601 can then carry out work, such as maintenance or cell/biomolecule harvesting on the culture within the bioreactor 1680. Once work has been completed, the user 1701 can close the sliding panel 1663b of the guard unit (FIG. 17) and raise the movable platform 1870 using the control panel 1869 to its return the bioreactor 1880 to its resting or storage position within the chamber 1864 of the guard unit 1860 of the system 1800. The guard unit 1960 can then be pushed back to partially surround or enclose the stacking unit 1940 and the wheels 1966 locked to secure it into position (FIG. 19). The system 1900 is now in a resting or storage position and, once reconnected to utilities and waste outlets, can be left in this position or configuration until further work is required on the cultures within the bioreactors.

Figure 20:
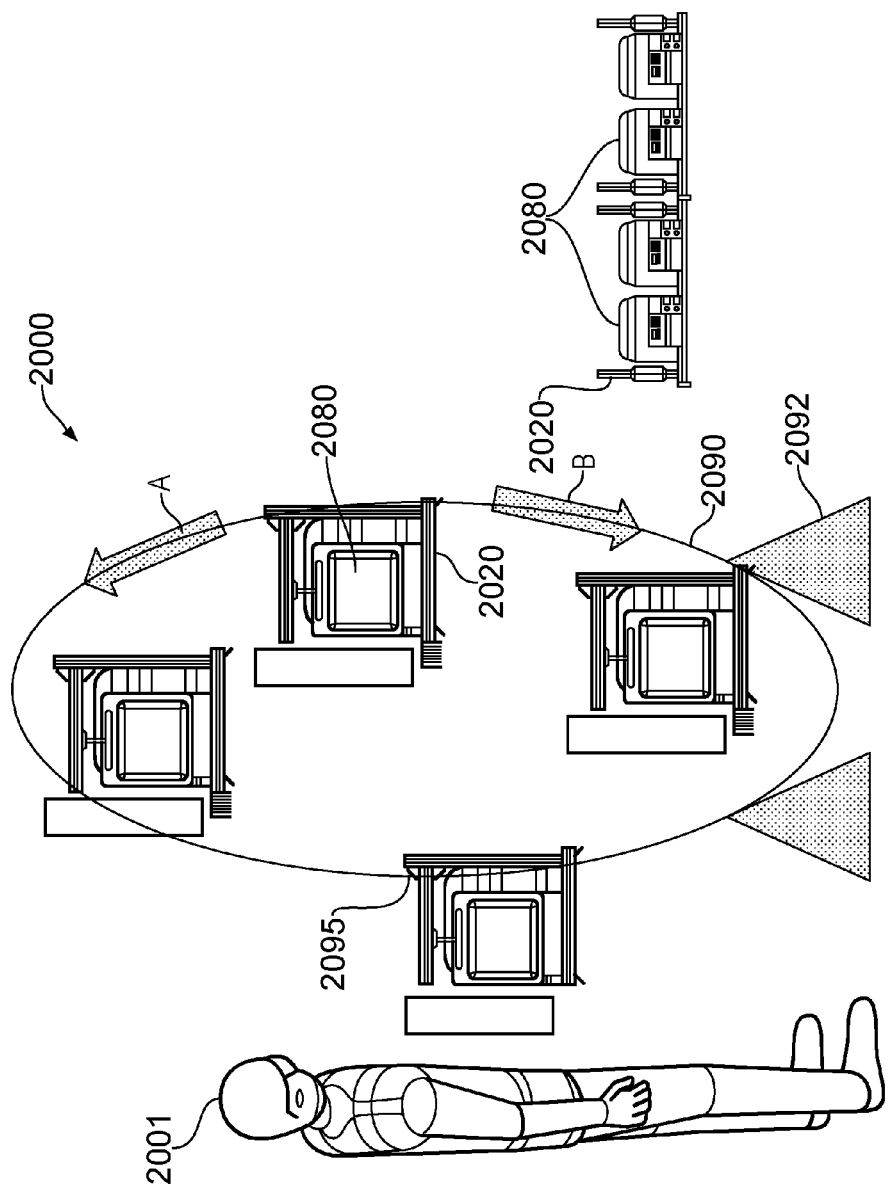
FIG. 20 is a schematic diagram showing a system 2000 for cell culture and/or biomanufacturing.

FIG. 20 is a schematic diagram showing a system 2000 for cell culture and/or biomanufacturing comprising a housing 2090 comprising a plurality of vertically stacked workstations 2020, a mechanism 2092 for rotating said plurality of workstations; and a port 2095 for providing user 2001 access to one of the workstations 2020. The system 2000 allows multiple workstations to be held per floor of space area (e.g. two, three, four, five, six or seven). The workstations 2020 are presented in an ergonomically suitable form for the user 2001. The rotating mechanism 2092 allows full rotation to each of the workstations 2020 either continuously or in a single rotation format (arrows A and B depict the direction of rotation). Each workstation 2020 has a suitable identification (e.g. bar code or RFID tag) so that the user 2001 can dial up or retrieve and access the workstation 2020 of interest. Moreover, each bioreactor 2080 is uniquely identified by, for example, a bar code or RFID tag).

While illustrative embodiments of the present invention are described, one skilled in the art will appreciate that the present invention can be practiced by other than the described embodiments, which are presented for purposes of illustration only and not by way of limitation. The present invention is limited only by the claims that follow.

What is claimed is:

1. A system for cell culture and/or biomanufacturing, the system comprising:
   a base unit comprising:
   a frame supporting walls and a movable platform to define a chamber therein;
   a stacking unit comprising:
   a frame supporting side walls, a back wall, a ceiling, and a movable platform to define an upper chamber and a lower chamber therein, wherein said lower chamber is dimensioned to receive said base unit therein; and
   a guard unit comprising:
   a frame supporting side walls, a movable platform, and an openable front wall to define an upper chamber and a lower chamber therein, wherein said lower chamber is dimensioned to partially receive said stacking unit therein; and
   legs supporting said frame and dimensioned to receive said base unit therebetween,
   wherein said base unit, said stacking unit, and said guard unit are interconnected to provide a plurality of workstations and/or storage bays for a bioreactor.

2. The system according to claim 1, wherein said base unit and/or said stacking unit and/or said guard unit are movable.

3. The system according to claim 2, wherein said base unit and/or said stacking unit and/or said guard unit comprise wheels.

4. The system according to claim 3, wherein said wheels are reversibly lockable.

5. The system according to claim 1, further comprising a connection to utilities selected from the group consisting of electricity, water, nitrogen, oxygen, air and carbon dioxide.

6. The system according to claim 1, further comprising a connection to a waste disposal outlet.

7. The system according to claim 1, further comprising a connection to a refrigeration unit.

8. The system according to claim 1, wherein said platform within said base unit is movable in a vertical plane.

9. The system according to claim 1, wherein said lower platform in said stacking unit is movable in a horizontal and/or a vertical plane.

10. The system according to claim 1, wherein said platform in said guard unit is movable in a horizontal and/or a vertical plane.

11. The system according to claim 1, wherein said openable front wall of said guard unit is a sliding wall.

12. The system according to claim 1, wherein said chamber of said base unit, said stacking unit, and said guard unit comprise internal sterilizable surfaces.

13. The system according to claim 1, wherein said base unit, said stacking unit, and said guard unit have a cuboid configuration.

14. The system according to claim 1, wherein at least one of said platform in said base unit and said platform in said stacking unit can support at least one bioreactor.

15. The system according to claim 14, wherein said bioreactor is a movement based bioreactor such as a WAVE bioreactor.

16. The system according to claim 14, wherein said bioreactor is a stir tank bioreactor.

17. The system according to claim 1, wherein at least one of said platforms is movable by an electronic device or a pneumatic device.

18. A method for cell culture, the method comprising:
   growing a cell culture in at least one bioreactor in a system according to claim 1 to produce a plurality of cells.

* * * * *